（12）United States Patent
Betsugi et al.

(10) Patent No.: US 12,082,891 B2
(45) Date of Patent: Sep. 10, 2024

(54) ROBOTIC SURGICAL APPARATUS, SURGICAL INSTRUMENT, AND METHOD OF ATTACHING SURGICAL INSTRUMENT TO ROBOT ARM

(71) Applicant: MEDICAROID CORPORATION, Kobe (JP)

(72) Inventors: Shota Betsugi, Kobe (JP); Yu Usuki, Kobe (JP); Kaoru Takahashi, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 777 days.

(21) Appl. No.: 17/073,431

(22) Filed: Oct. 19, 2020

(65) Prior Publication Data

US 2021/0113283 A1 Apr. 22, 2021

(30) Foreign Application Priority Data

Oct. 21, 2019 (JP) ................................ 2019-192313

(51) Int. Cl.
*A61B 34/30* (2016.01)
*A61B 1/00* (2006.01)
*A61B 18/14* (2006.01)

(52) U.S. Cl.
CPC .......... *A61B 34/30* (2016.02); *A61B 1/00149* (2013.01); *A61B 18/14* (2013.01);
(Continued)

(58) Field of Classification Search
CPC ...... A61B 34/30; A61B 1/00149; A61B 18/14
See application file for complete search history.

(56) References Cited

U.S. PATENT DOCUMENTS

2006/0235436 A1 10/2006 Anderson et al.
2016/0361131 A1 12/2016 Dachs, II et al.
(Continued)

FOREIGN PATENT DOCUMENTS

JP 5403864 B2 1/2014
KR 10-2011-0032444 A 3/2011
(Continued)

*Primary Examiner* — Lynsey C Eiseman
*Assistant Examiner* — Daniel Tehrani
(74) *Attorney, Agent, or Firm* — METROLEX IP LAW GROUP, PLLC

(57) ABSTRACT

A patient-side apparatus according an embodiment may include a robot arm; an adaptor that is attached to the robot arm; and a surgical instrument that is attached to the adaptor by sliding the surgical instrument to the adaptor. The adaptor includes: an adaptor base including an arm attachment surface and a surgical instrument attachment surface; a drive transmission member provided being movable in a direction perpendicular to the surgical instrument attachment surface and configured to transmit a driving force from the robot arm to the surgical instrument. The surgical instrument includes a surgical instrument base including an adaptor attachment surface. The surgical instrument base includes an inclined surface configured, upon slide attachment of the surgical instrument to the adaptor, to come in contact with the drive transmission member to move the drive transmission member toward the robot arm side in a direction perpendicular to the surgical instrument attachment surface.

20 Claims, 8 Drawing Sheets

(52) U.S. Cl.
CPC ... *A61B 1/00045* (2013.01); *A61B 2018/1412* (2013.01); *A61B 2034/301* (2016.02)

(56) References Cited

U.S. PATENT DOCUMENTS

| | | |
|---|---|---|
| 2018/0168753 A1 | 6/2018 | Scheib et al. |
| 2020/0061847 A1* | 2/2020 | Dixon .................... A61B 34/30 |

FOREIGN PATENT DOCUMENTS

| | | | |
|---|---|---|---|
| WO | 2007/142698 A2 | 12/2007 | |
| WO | WO-2011037394 A2 * | 3/2011 | ............. A61B 17/00 |
| WO | 2015/023853 A1 | 2/2015 | |

* cited by examiner

ROBOTIC SURGICAL APPARATUS, SURGICAL INSTRUMENT, AND METHOD OF ATTACHING SURGICAL INSTRUMENT TO ROBOT ARM

CROSS REFERENCE TO RELATED APPLICATIONS

This application claims priority to Japanese Patent Application No. 2019-192313 filed on Oct. 21, 2019, the entire contents of which are incorporated herein by reference.

BACKGROUND

The disclosure may relate to a robotic surgical apparatus and a surgical instrument, and may particularity relate to a robotic surgical apparatus including a surgical instrument to be slidably attached to adaptor mounted to a robot arm, a surgical instrument, and a method of attaching a surgical instrument to a robot arm.

There has been known a surgical instrument that is to be attached to an adaptor mounted to a robot arm by sliding the surgical instrument with respect to the adaptor.

Japanese Patent No. 5,403,864 discloses a surgical instrument that is attached to an adaptor mounted to a robot arm by sliding the surgical instrument with respect to the adaptor. The adaptor includes a disk to transmit a driving force to the surgical instrument. The disk of the adaptor is protruded toward the surgical instrument side beyond a surgical instrument attachment surface of the adaptor.

SUMMARY

In the case where the disk protrudes toward the surgical instrument side from the surgical instrument attachment surface of the adaptor as in the adaptor disclosed in Japanese Patent No. 5,403,864, the protruded disk causes a resistance when the surgical instrument is slid to be attached to the adaptor, so that a force required for attaching the surgical instrument to the adaptor may be increased. In this case, it may be difficult to smoothly attach the surgical instrument to the adaptor.

An object of an embodiment of the disclosure may be to provide a robotic surgical apparatus and a surgical instrument that allow the surgical instrument to be smoothly attached to an adaptor.

A first aspect of the disclosure may be a robotic surgical apparatus that include: a robot arm; an adaptor that is attached to the robot arm; and a surgical instrument that is attached to the adaptor by sliding the surgical instrument with respect to the adaptor. The adaptor includes: an adaptor base including an arm attachment surface attached to the robot arm, a surgical instrument attachment surface which is provided on an opposite side of the arm attachment surface and to which the surgical instrument is attached; a drive transmission member provided being movable in a direction perpendicular to the surgical instrument attachment surface of the adaptor base and configured to transmit a driving force from the robot arm to the surgical instrument. The surgical instrument includes a surgical instrument base including an adaptor attachment surface to be attached to the adaptor. The surgical instrument base includes an inclined surface configured, upon the slide attachment of the surgical instrument to the adaptor, to come in contact with the drive transmission member to move the drive transmission member toward the robot arm side in the direction perpendicular to the surgical instrument attachment surface of the adaptor.

A second aspect of the disclosure may be a surgical instrument to be attached to a surgical instrument attachment surface of an adaptor provided on an opposite side of an arm attachment surface of the adaptor attached to a robot arm, by sliding the surgical instrument with respect to the adaptor. The surgical instrument includes a surgical instrument base including an adaptor attachment surface to be attached to the adaptor. The surgical instrument base includes an inclined surface configured, upon the slide attachment of the surgical instrument to the adaptor, to come in contact with a drive transmission member to move the drive transmission member toward the robot arm side in a direction perpendicular to the surgical instrument attachment surface of the adaptor, wherein the drive transmission member is provided being movable in the direction perpendicular to the surgical instrument attachment surface of the adaptor and configured to transmit a driving force from the robot arm to the surgical instrument.

A third aspect of the disclosure may be a method of attaching a surgical instrument to an adaptor attached to a robot arm, by sliding the surgical instrument with respect to the adaptor.

The method may include: guiding the surgical instrument by a precedent guide portion protruded from an adaptor base of the adaptor toward a direction opposite to a direction of the slide attachment of the surgical instrument to the adaptor; and bringing an inclined surface of the surgical instrument into contact with a drive transmission member provided to the adaptor base and configured to transmit a driving force from the robot arm to the surgical instrument, to move the drive transmission member in a direction perpendicular to the surgical instrument attachment surface of the adaptor.

DETAILED DESCRIPTION

Figure 1:
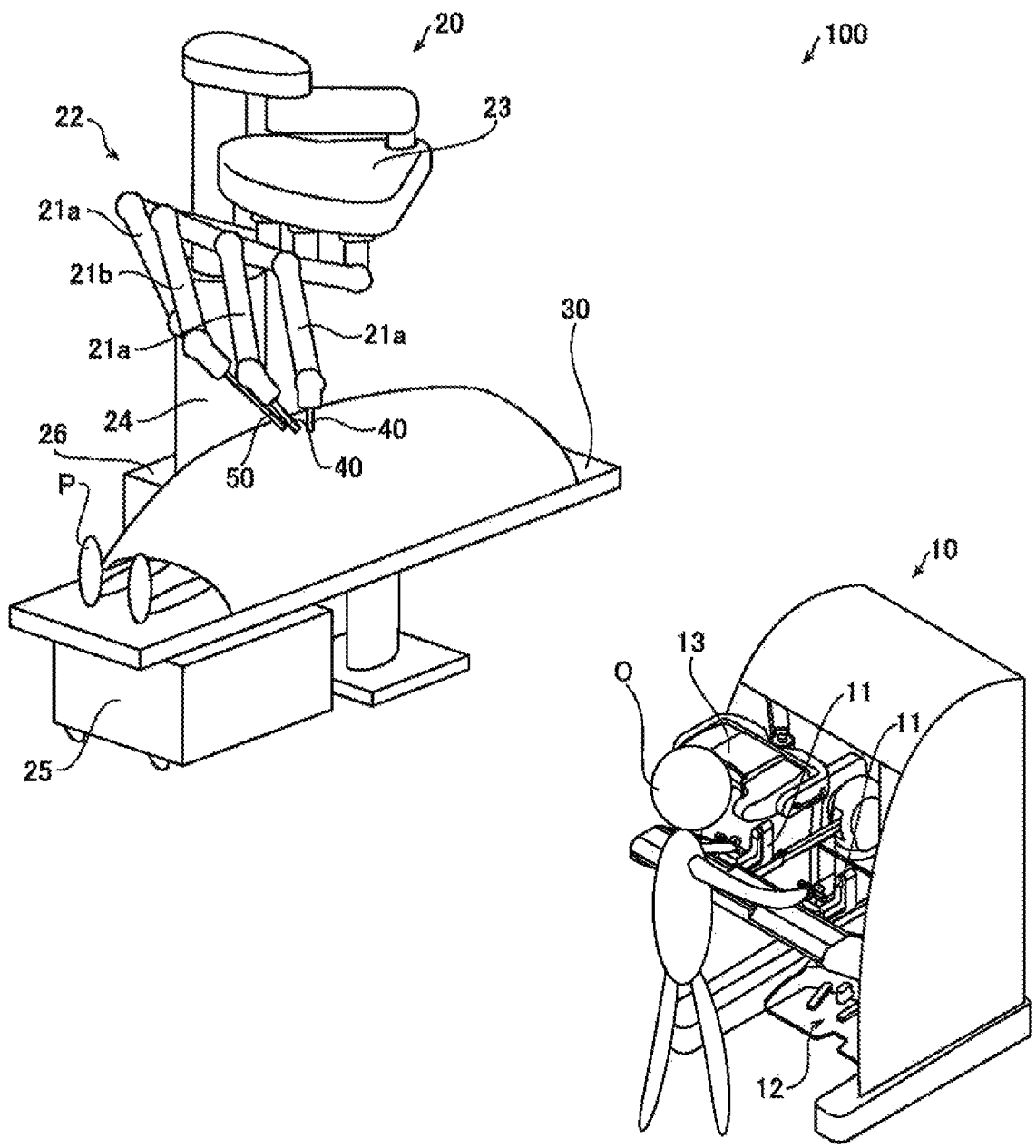
FIG. 1 is a diagram illustrating an overview of a robotic surgical system according to an embodiment.

Descriptions are provided hereinbelow for one or more embodiments based on the drawings. In the respective drawings referenced herein, the same constituents are designated by the same reference numerals and duplicate explanation concerning the same constituents is omitted. All of the drawings are provided to illustrate the respective examples only.

(Configuration of Robotic Surgical System)

A configuration of a robotic surgical system 100 according to an embodiment is described with reference to FIGS. 1 and 2.

As illustrated in FIG. 1, the robotic surgical system 100 includes a remote control apparatus 10 and a patient-side apparatus 20.

The remote control apparatus 10 is provided to remotely control medical equipment provided to the patient-side apparatus 20. When an operator O, as a surgeon, inputs an action mode instruction to be executed by the patient-side apparatus 20, to the remote control apparatus 10, the remote control apparatus 10 transmits the action mode instruction to the patient-side apparatus 20 through a controller 26. In response to the action mode instruction transmitted from the remote control apparatus 10, the patient-side apparatus 20 operates medical equipment such as surgical instruments 40, an endoscope 50, and the like, attached to robot arms 21a and 21b. This allows for minimally invasive surgery. The patient-side apparatus 20 is an example of a robotic surgical apparatus.

The patient-side apparatus 20 constitutes an interface to perform a surgery for a patient P. The patient-side apparatus 20 is positioned beside an operation table 30 on which the patient P is laid.

The patient-side apparatus 20 includes plural robot arms 21a and 21b. One of the robot arms 21b holds the endoscope 50 while the other robot arms 21a hold the surgical instruments 40. The robot arms 21a and 21b are commonly supported by a platform 23. Each of the robot arms 21a and 21b includes plural joints. Each joint includes a driver provided with a servo-motor and a position detector such as an encoder. The robot arms 21a and 21b are configured so that the medical equipment attached to each of the robot arms 21a and 21b is controlled by a driving signal given through the controller 26 and performs a desired movement.

The platform 23 is supported by a positioner 22 placed on the floor of an operation room. The positioner 22 includes a column 24 and a base 25. The column 24 includes an elevating shaft adjustable in the vertical direction. The base 25 includes wheels and is movable on the floor surface.

The surgical instruments 40 as the medical equipment is detachably attached to the distal ends of the robot arms 21a. The surgical instrument 40 is a surgical instrument that is detachably connected to the robot arm 21a of the robotic surgical system 100 through the adaptor 60 (see FIG. 3). As illustrated in FIG. 4, the surgical instrument 40 includes a base 40b formed with an adaptor attachment surface 40a which is to be attached to the adaptor 60, an elongate shaft 42 whose one end is connected to the base 40b, and an end effector 41 connected to the other end of the shaft 42. The end effector 41 is grasping forceps, scissors, a hook, a high-frequency knife, a snare wire, a clamp, or a stapler, for example. The end effector 41 is not limited to those and can be various types of treatment tools. In surgeries using the patient-side apparatus 20, the robot arms 21a introduce the surgical instruments 40 into the body of the patient P through a cannula (trocar) placed on the body surface of the patient P. The end effectors 41 of the surgical instruments 40 are then located near the surgery site. A base 40b is an example of a base of the surgical instrument or a surgical instrument base.

To the distal end of the robot arm 21b, the endoscope 50 as the medical equipment is detachably attached. The endoscope 50 captures an image in a body cavity of the patient P. The captured image is outputted to the remote control apparatus 10. The endoscope 50 is a 3D endoscope capable of capturing a three-dimensional image or a 2D endoscope. In surgeries using the patient-side apparatus 20, the robot arm 21b introduces the endoscope 50 into the body of the patient P through a trocar placed on the body surface of the patient P. The endoscope 50 is then located near the surgery site.

The remote control apparatus 10 constitutes the interface with the operator O. The remote control apparatus 10 is an apparatus that allows the operator O to operate the medical equipment attached to the robot arms 21a and 21b. Specifically, the remote control apparatus 10 is configured to transmit action mode instructions which are inputted by the operator O and are to be executed by the surgical instruments 40 and endoscope 50, to the patient-side apparatus 20 through the controller 26. The remote control apparatus 10 is installed beside the operation table 30 so that the operator O can see the condition of the patient P very well while operating the remote control apparatus 10, for example. The remote control apparatus 10 may be configured to transmit action mode instructions wirelessly and installed in a room different from the operation room where the operation table 30 is installed.

The action modes to be executed by the surgical instruments 40 include modes of actions to be taken by each surgical instrument 40 (a series of positions and postures) and actions to be executed by the function of each surgical instrument 40. When the surgical instrument 40 is a pair of grasping forceps, for example, the action modes to be executed by the surgical instrument 40 include roll and pitch positions of the wrist of the end effector 41 and actions to open and close the jaws. When the surgical instrument 40 is a high-frequency knife, the action modes to be executed by the surgical instrument 40 include vibration of the high-frequency knife, specifically, supply of current to the high-frequency knife. When the surgical instrument 40 is a snare wire, the action modes to be executed by the surgical instrument 40 include a capturing action and an action to release the captured object. Further the action modes may include an action to supply current to a bipolar or monopolar instrument to burn off the surgery site.

The action modes to be executed by the endoscope 50 include the position and posture of the tip of the endoscope 50 and setting of the zoom magnification, for example.

Figure 2:
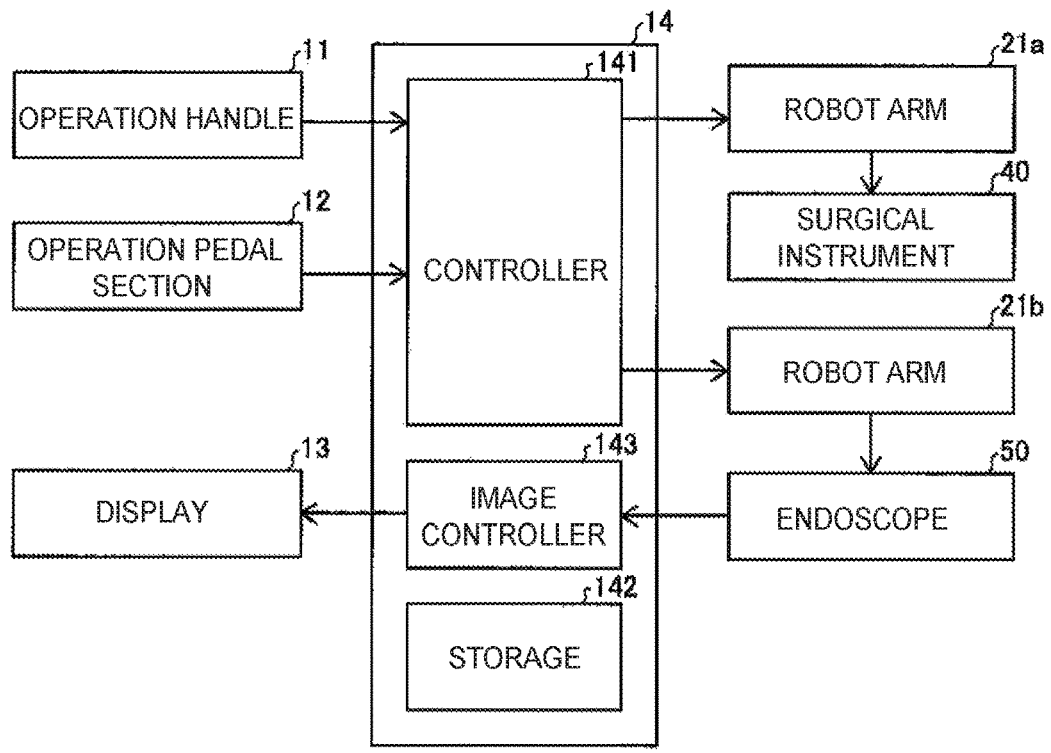
FIG. 2 is a block diagram illustrating a view of a control-related configuration of the robotic surgical system according to an embodiment.

As illustrated in FIGS. 1 and 2, the remote control apparatus 10 includes operation handles 11, an operation pedal section 12, a display 13, and a control apparatus 14.

The operation handles 11 are provided in order to remotely operate medical equipment attached to the robot arms 21a and 21b. Specifically, the operation handles 11 accept operations by the operator O for operating the medical equipment (the surgical instruments 40 and endoscope 50). The operation handles 11 include two operation handles 11 arranged side by side in the horizontal direction. One of the two operation handles 11 is operated by the right hand of the operator O while the other operation handle 11 is operated by the left hand of the operator O.

The operation handles 11 extend from the rear side of the remote control apparatus 10 toward the front side. The operation handles 11 are configured to move in a predetermined three-dimensional operation region. Specifically, the operation handles 11 are configured so as to move up and down, right and left, and forward and rearward.

The remote control apparatus 10 and patient-side apparatus 20 constitute a master-slave system in terms of controlling movement of the robot arms 21a and robot arm 21b. The operation handles 11 constitute an operating section or an operating part on the master side in the master-slave system, and the robot arms 21a and 21b holding the medical equipment constitute an operating section or an operation part on the slave side. When the operator O operates the operation handles 11, the movement of one of the robot arms 21a or 21b is controlled so that the distal end portion (the end effector 41 of the surgical instrument 40) of the robot arm 21a or the distal end portion (the endoscope 50) of the robot arm 21b moves following the movement of the operation handles 11.

The patient-side apparatus 20 controls the movement of the robot arms 21a in accordance with the set motion scaling ratio. When the motion scaling ratio is set to ½, for example, the end effectors 41 of the surgical instruments 40 move ½ of the movement distance of the operation handles 11. This allows for precise fine surgery.

The operation pedal section 12 or an operation pedal unit includes plural pedals to execute medical equipment-related functions. The plural pedals include a coagulation pedal, a cutting pedal, a camera pedal, and a clutch pedal. The plural pedals are operated by a foot of the operator O.

The coagulation pedal enables the surgical instrument 40 to coagulate a surgery site. Specifically, when the coagulation pedal is operated, voltage for coagulation is applied to the surgical instrument 40 to coagulate a surgery site. The cutting pedal enables the surgical instrument 40 to cut a surgery site. Specifically, the cutting pedal is operated to apply voltage for cutting to the surgical instrument 40 and cut a surgery site.

The camera pedal is used to control the position and orientation of the endoscope 50 that captures images within the body cavity. Specifically, the camera pedal enables operation of the endoscope 50 by the operation handles 11. That is, the position and orientation of the endoscope 50 are controllable by the operation handles 11 while the camera pedal is being pressed. The endoscope 50 is controlled by using both of the right and left operation handles 11, for example. Specifically, when the operator O rotates the right and left operation handles 11 about the middle point between the right and left operation handles 11, the endoscope 50 is rotated. When the operator O presses the right and left operation handles 11 together, the endoscope 50 goes forward into the body cavity. When the operator O pulls the right and left operation handles 11 together, the endoscope 50 goes back. When the operator O moves the right and left operation handles 11 together up, down, right, or left, the endoscope 50 moves up, down, right, or left, respectively.

The clutch pedal is used to temporarily disconnect operation-related connection between the operation handles 11 and the robot arms 21a to stop movement of the surgical instruments 40. Specifically, when the clutch pedal is being pressed, the robot arms 21a of the patient-side apparatus 20 do not work even if the operation handles 11 are operated. For example, when the operation handles 11 are operated and moved to the edge of the range of movement, the operator O operates the clutch pedal to temporarily disconnect the operation-related connection and then returns the operation handles 11 to the center of the range of movement. When the operator O stops operating the clutch pedal, the operation handles 11 are again connected to the robot arms 21a. The operator O restarts the operation for the operation handles 11 around the center thereof.

The display 13 or a display unit is configured to display images captured by the endoscope 50. The display 13 includes a scope type display or a non-scope type display. The scope type display is a display that the operator O looks into. The non-scope type display is a display like an open-type display that includes a flat screen and the operator O is able to see without looking into, such as normal displays for personal computers.

When the scope type display is attached, the scope type display displays 3D images captured by the endoscope 50 attached to the robot arm 21b of the patient-side apparatus 20. When the non-scope type display is attached, the non-scope type display also displays 3D images captured by the endoscope 50 provided for the patient-side apparatus 20. The non-scope type display may display 2D images captured by the endoscope 50 provided for the patient-side apparatus 20.

As illustrated in FIG. 2, the control apparatus 14 includes a controller 141, a storage 142, and an image controller 143, for example. The controller 141 includes a calculator such as a CPU. The storage 142 includes a memory, such as a ROM and a RAM. The control apparatus 14 may be composed of a single controller performing centralized control or may be composed of plural controllers that perform decentralized control in cooperation with each other. The controller 141 determines whether an action mode instruction inputted by the operation handles 11 is to be executed by the robot arms 21a or to be executed by the endoscope 50, depending on the state of the operation pedal section 12. When determining that the action mode instruction inputted by the operation handles 11 is to be executed by any one of the surgical instruments 40, the controller 141 transmits the action mode instruction to the corresponding robot arm 21a. The robot arm 21a is thereby driven for controlling movement of the surgical instrument 40 attached to the robot arm 21a.

When determining that the action mode instruction inputted by the operation handles 11 is to be executed by the endoscope 50, the controller 141 transmits the action mode instruction to the robot arm 21b. The robot arm 21b is thereby driven for control of movement of the endoscope 50 attached to the robot arm 21b.

The storage 142 stores control programs corresponding to the types of the surgical instrument 40, for example. The controller 141 reads the stored control programs according to the types of the attached surgical instruments 40. The action mode instructions from the operation handles 11 and/or the operation pedal section 12 of the remote control apparatus 10 thereby cause the respective surgical instruments 40 to perform proper movements.

The image controller 143 transmits images acquired by the endoscope 50 to the display 13. The image controller 143 performs processing and alternations for the images when needed.

(Configurations of Adaptor and Surgical Instrument)

With reference to FIGS. 3 to 10, the configurations of the adaptor 60 and the surgical instrument 40 according to an embodiment are described.

Figure 3:
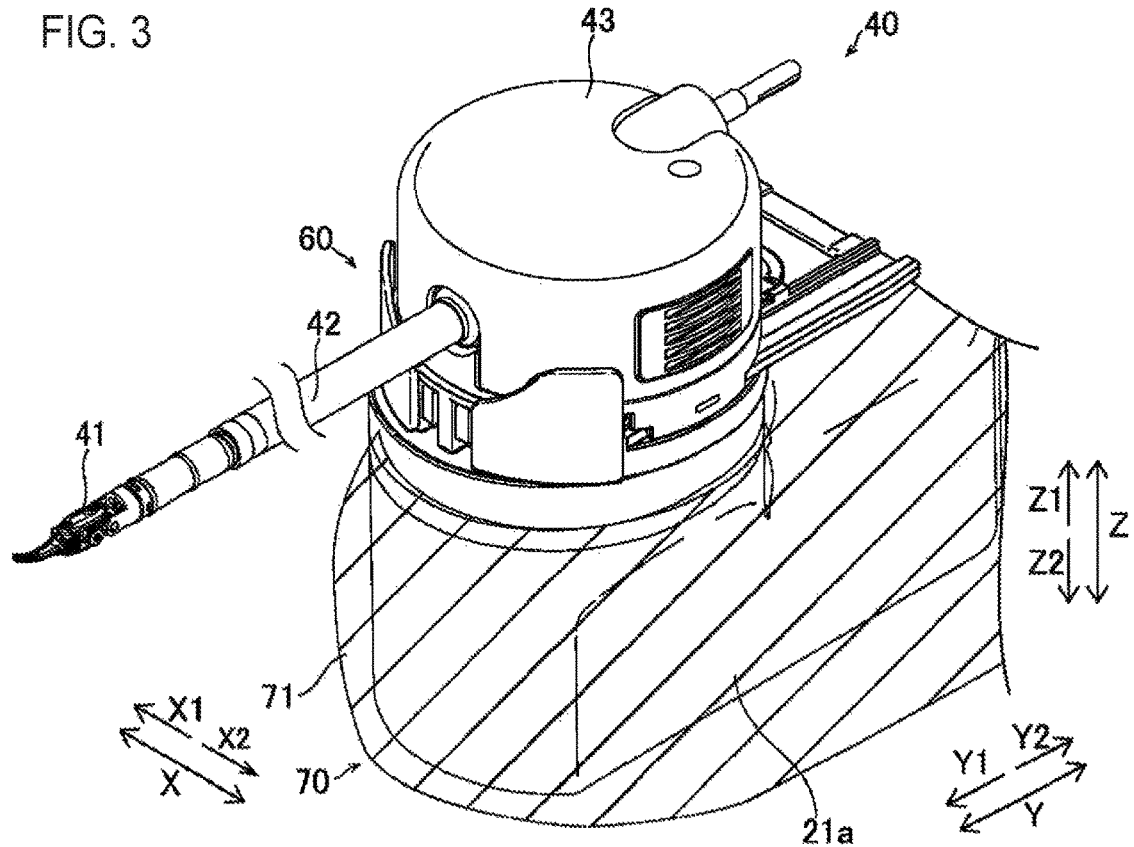
FIG. 3 is a diagram illustrating a perspective view of a state where a surgical instrument is attached to a robot arm through an adaptor according to an embodiment.
Figure 4:
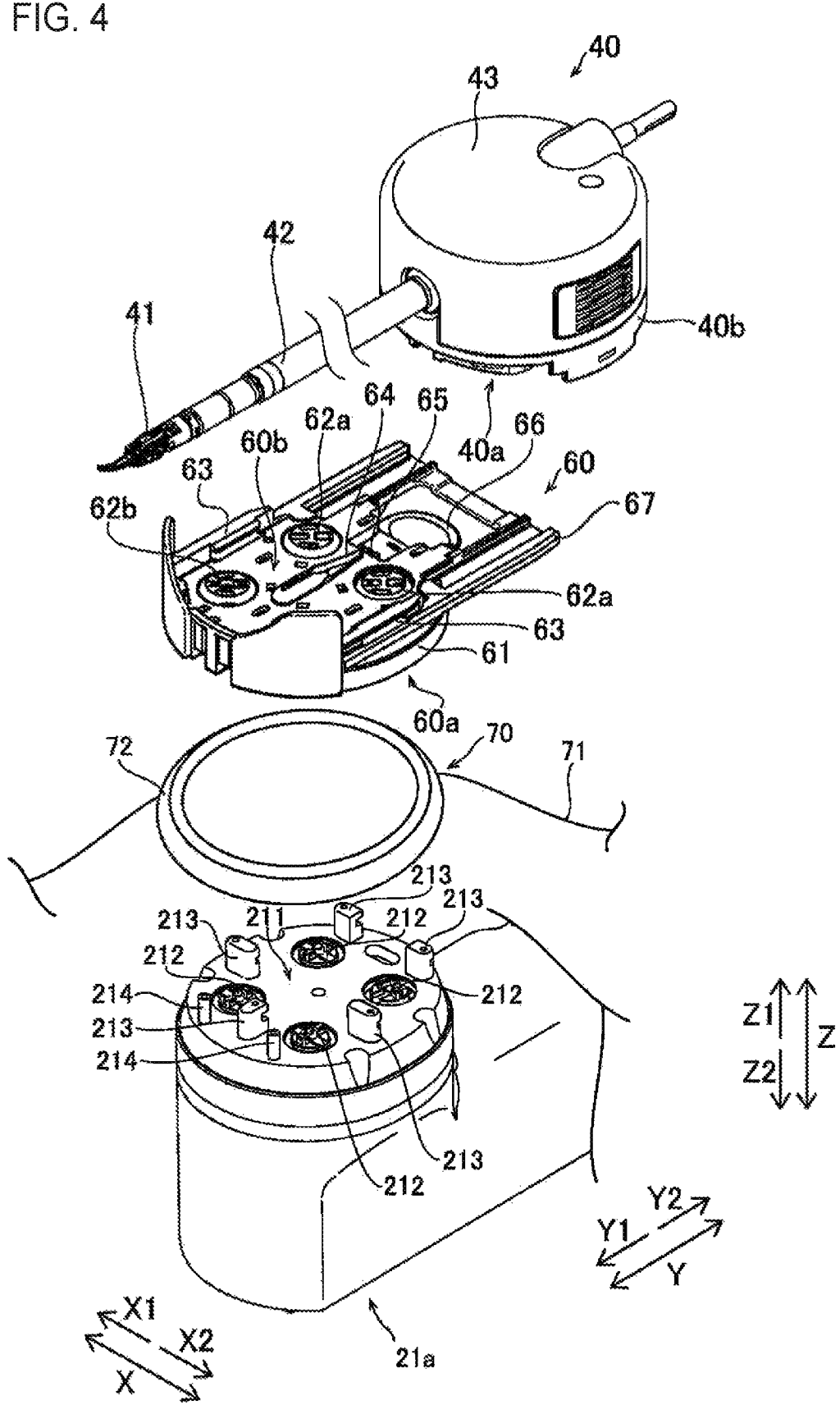
FIG. 4 is a diagram illustrating a perspective view of a state where the adaptor and the surgical instrument are detached from the robot arm according to an embodiment.

As illustrated in FIG. 3, the robot arm 21a is to be used in a clean area and is thus covered with a drape 70. In operation rooms, clean technique is used in order to prevent surgical incision sites and the medical equipment from being contaminated by pathogen, foreign matters, or the like. The clean technique defines a clean area and a contaminated area, which is other than the clean area. The surgery sites are located in the clean area. Members of the surgical team, including the operator O, make sure that only sterile objects are placed in the clean area during surgery and perform sterilization for an object which is to be moved to the clean area from the contaminated area. Similarly, when the members of the surgical team including the operator O place their hands in the contaminated area, the members sterilize their hands before directly touching objects located in the clean area. Instruments used in the clean area are sterilized or are covered with sterile drape 70.

The drape 70 is arranged between the robot arm 21a and the surgical instrument 40. Specifically, the drape 70 is arranged between the adaptor 60 and the robot arm 21a. Further, the drape 70 is arranged between the robot arm 21b and the endoscope 50. The adaptor 60 is attached to the robot arm 21a while putting the drape 70 between the adaptor 60 and the robot arm 21a. Specifically, the adaptor 60 is a drape adaptor that puts the drape 70 between the adaptor 60 and the robot arm 21a. The drape 70 is thus able to be mounted through the adaptor 60. The surgical instrument 40 is attached to the adaptor 60 that is attached to the robot arm 21a with the drape 70 interposed therebetween. The robot arm 21a transmits driving force to the surgical instrument 40 through the adaptor 60 to drive the end effector 41 of the surgical instrument 40.

Figure 5:
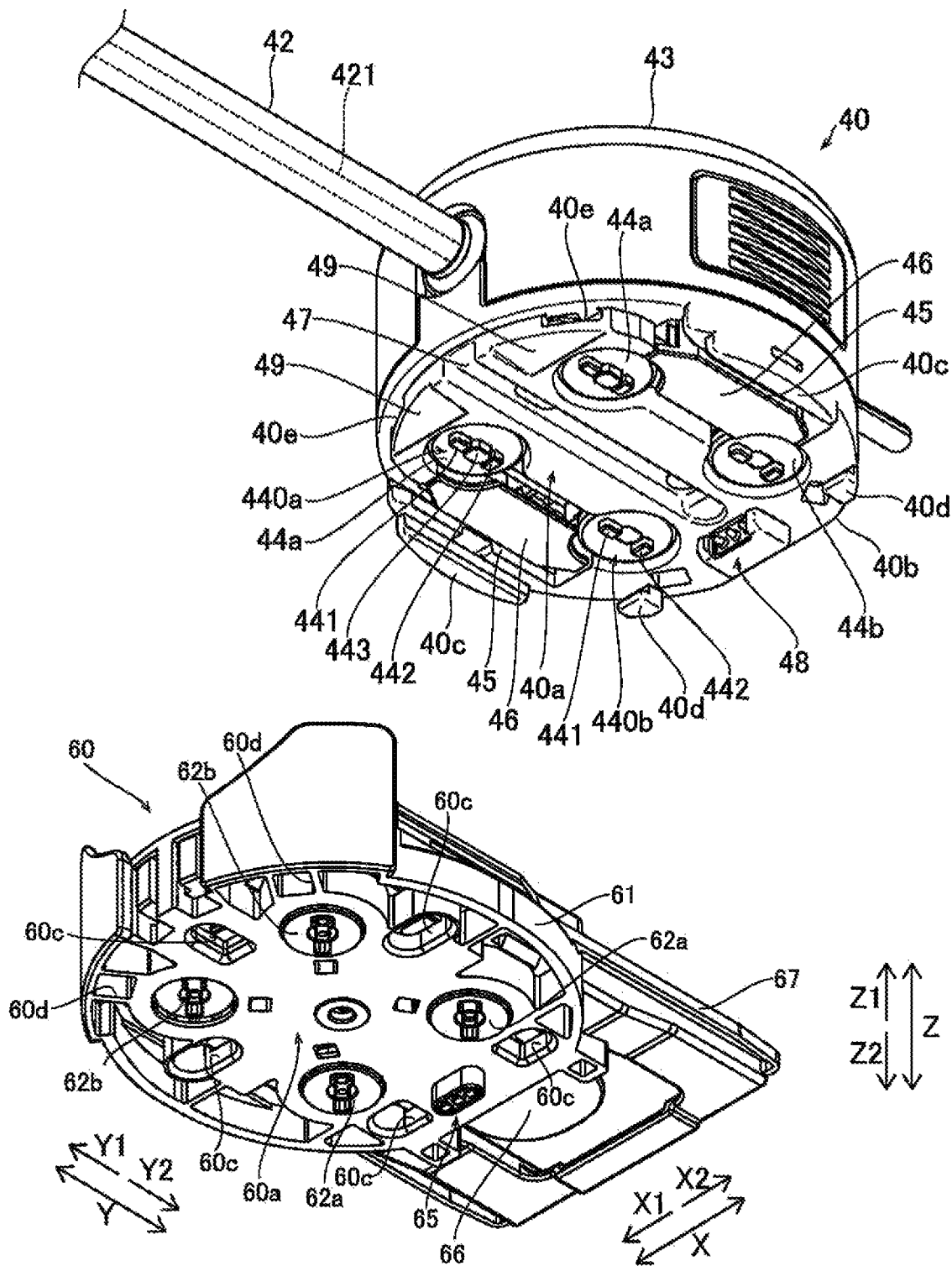
FIG. 5 is a diagram illustrating a perspective view of the adaptor and the surgical instrument according to an embodiment as seen from below.

As illustrated in FIG. 4, the adaptor 60 is attached to the robot arm 21a. The adaptor 60 includes: a base 61 formed with an arm attachment surface 60a and a surgical instrument attachment surface 60b; a plurality of drive transmission members 62a and 62b; a pair of guide rails 63; a precedence guide rail 64; an electrode array 65; an arm engagement portion 66; a precedence guide portion 67; a pair of engagement holes 68 (see FIG. 10); and a pair of engagement tabs 69 (see FIG. 10). As illustrated in FIG. 5, the adaptor 60 includes arm engagement holes 60c and positioning holes 60d. As illustrated in FIG. 4, among the drive transmission members 62a and 62b, the drive transmission members 62a are arranged on the Y2 side and the drive transmission members 62b are arranged on the Y1 side. The adaptor 60 includes an arm attachment surface 60a arranged on the Z2 side thereof such that the arm attachment surface 60a of the adaptor 60 is attached to the robot arm 21a. The surgical instrument 40 is attached to the surgical instrument attachment surface 60b of the adaptor 60, which is provided on the Z1 side (on the side opposite to the arm attachment surface 60a). Note that the base 61 is an example of a base of the adaptor or an adaptor base. The engagement hole 68 is an example of a first engagement portion of the adaptor or a first adaptor side engagement portion. The engagement tab 69 is an example of a second engagement portion of the adaptor or a second adaptor side engagement portion.

The surgical instrument 40 is a surgical instrument that is detachably connected to the robot arm 21a of the robotic surgical system 100 through the adaptor 60. The surgical instrument 40 is attached to the adaptor 60 by sliding the surgical instrument with respect to the adaptor. A direction (Y1) in which the surgical instrument 40 is slid to be attached to the adaptor 60 (a slide attachment direction) is substantially parallel to a direction in which the shaft 42 of the surgical instrument 40 extends. With this, unlike the slide attachment direction extends in a direction intersecting with the extending direction of the shaft 42, a space needed to move the shaft 42 upon slidably attaching the surgical instrument 40 to the adaptor 60 may be provided only in the extending direction of the shaft 42. That is, it is not needed to enlarge the space for moving the shaft 42 in the direction intersecting with the extending direction of the shaft 42.

As illustrated in FIG. 5, the adaptor attachment surface 40a arranged in the Z2 side of the housing 43 of the surgical instrument 40 is attached to the adaptor 60. The surgical instrument 40 includes driven members 44a and 44b, a pair of guide grooves 45, a pair of movable members 46, a precedence guide groove 47, an electrode array 48, and a pair of inclined surfaces 49. The surgical instrument 40 also includes a pair of guided portions 40c, a pair of engagement tabs 40d, and a pair of engagement holes 40e. Among the driven members 44a and 44b, the driven members 44a are arranged on the Y1 side and the driven members 44b are arranged on the Y2 side. The surgical instrument 40 includes the base 40b that includes the adaptor attachment surface 40a, which is an attachment surface to be attached to the adaptor 60. The inclined surface 49 is an example of an inclined surface of the surgical instrument or a surgical instrument side inclined surface. The engagement tab 40d is an example of a first engagement portion of the surgical instrument or a first surgical instrument side engagement portion. The engagement hole 40e is an example of a second engagement portion of the surgical instrument or a second surgical instrument side engagement portion.

As illustrated in FIG. 4, the drape 70 includes a body part 71 and an attachment section 72. The body part 71 is made in a film form. The attachment section 72 is made by resin molding. The attachment section 72 includes a through-opening at a portion where the robot arm 21a is engaged with the adaptor 60. The through-opening may be provided corresponding to each of plural engagement portions. Through-openings may be provided corresponding to plural engagement portions.

The adaptor 60 is attached to an adaptor attachment surface 211 of the robot arm 21a. The robot arm 21a includes rotation drive parts 212, engagement portions 213, and bosses 214.

As illustrated in FIG. 5, the driven members 44a and 44b of the surgical instrument 40 are driven to be rotated to drive the end effector 41. Specifically, one end (an end portion on the Y2 side) of the shaft 42 is connected to the base 40b, and the other end (an end portion on the Y1 side) of the shaft 42 is connected to the end effector 41. The driven members 44a and 44b are rotatably provided on the base 40b. One or more of the driven members 44a and 44b are connected to the end effector 41 with wires 421 inserted through the shaft 42. Specifically, end portions of the wires 421 for operating the end effector 41 are connected to the one or more of the driven members 44a and 44b, respectively. When the one or more of the driven members 44a and 44b are rotated, the wires 421 are drawn to drive the end effector 41. In the housing 43, one or more of the driven members 44a and 44b are connected to the shaft 42 through gears, so that when the one or more of the driven members 44a and 44b are rotated, the shaft 42 is rotated. The housing 43 is provided on the base 40b to cover the driven members 44a and 44b.

As illustrated in FIG. 5, for example, the number of the driven members 44a provided is two. The number of the driven members 44b provided is two. When one of the driven members 44a is rotated, the shaft 42 is rotated. When one or more of the other three driven members 44a and 44b are rotated, the end effector 41 is driven. The four driven members 44a and 44b are arranged with two rows (column) in the X direction and two column (rows) in the Y direction.

Figure 6:
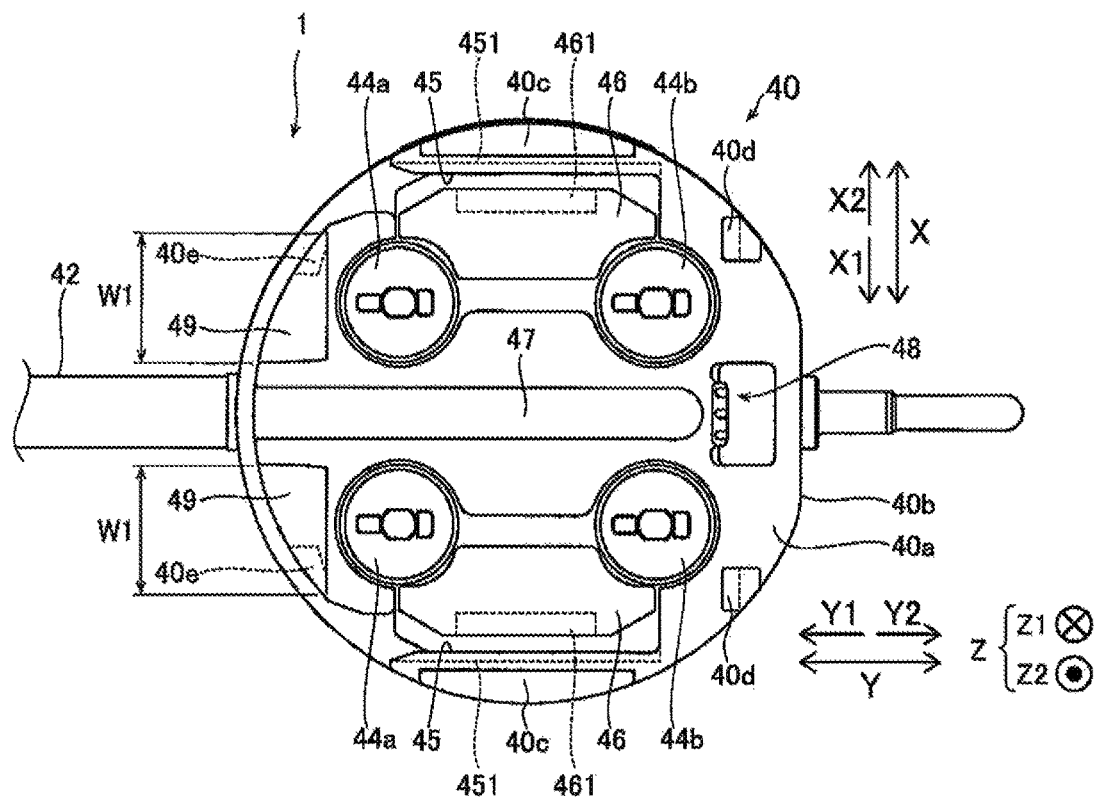
FIG. 6 is a diagram illustrating a plan view of the surgical instrument according to an embodiment as seen from the Z2 side.

As illustrated in FIGS. 5 and 6, the driven members 44a respectively include engagement portions 440a that are engaged with the corresponding drive transmission members 62b provided in the adaptor 60. The driven members 44b respectively include engagement portions 440b that are engaged with the corresponding drive transmission members 62a provided in the adaptor 60. The engagement portions 440a are respectively provided the driven members 44a on the Y1 side (a leading side of the slide attachment direction). The engagement portions 440b are respectively provided the driven members 44b on the Y2 side (a side opposite to the slide attachment direction or a tail side of the slide attachment direction). The engagement portion 440a has a shape different from that of the engagement portion 440b.

Specifically, the engagement portion 440a includes a first projection 441, a second projection 442 provided separately from the first projection 441, and a third projection 443 arranged between the first projection 441 and the second projection 442. The engagement portion 440b includes no third projection 443 and includes the first projection 441 and the second projection 442.

The pair of guide grooves 45 is provided on the adaptor attachment surface 40a of the base 40b. The pair of guide grooves 45 is provided to slidably receive the pair of guide rails 63 provided on the adaptor 60 respectively. Each of the guide grooves 45 is provided to extend along the Y direction. The guide grooves 45 are provided to be opposed to each other in the X direction. The pair of guide grooves 45 is provided substantially parallel to each other. The pair of guide grooves 45 is respectively inserted to the pair of guide rails 63 of the adaptor 60, to guide attachment of the surgical instrument 40 to the adaptor 60.

Each of the guide grooves 45 is at least partially defined by the corresponding movable member 46. Specifically, each of the guide grooves 45 is defined by the base 40b and the corresponding movable member 46. The movable members 46 are provided on the base 40b to be movable with respect to the base 40b. The movable members 46 are configured, when being moved with respect to the base 40b, to release the engagement with the adaptor 60. The movable members 46 are configured to be moved to change groove widths of the guide grooves 45. Specifically, the width of each guide groove 45 is varied according to movement in the X direction of the corresponding movable member 46. That is, when the movable member 46 is moved inward, the width of the guide groove 45 is increased. When the movable member 46 is moved outward, the width of the guide groove 45 is decreased. The movable member 46 is biased to a direction (an outward direction) in which the width of the guide groove 45 is decreased.

The precedence guide groove 47 is provided on the adaptor attachment surface 40a of the base 40b. The precedence guide groove 47 is provided to extend along the Y direction. The precedence guide groove 47 is provided between the pair of guide grooves 45. The precedence guide groove 47 is formed to extend substantially parallel to the pair of guide grooves 45. The precedence guide groove 47 is provided in the substantial center in the X direction of the adaptor attachment surface 40a.

The electrode array 48 is connected to the robot arm 21a through the electrode array 65 of the adaptor 60. The electrode array 48 is connected to a board (a circuit board or the like) provided in the housing 43. Specifically, the board of the surgical instrument 40 is connected to the robot arm 21a by attaching the surgical instrument 40 to the robot arm 21a through the adaptor 60. The board in the housing 43 is used for, for example, managing types of the surgical instrument 40 and the number of uses of the surgical instrument 40.

The pair of inclined surfaces 49 is provided on the adaptor attachment surface 40a of the base 40b. Specifically, the pair of inclined surfaces 49 is provided at a portion of the adaptor attachment surface 40a of the base 40b on the leading side (the Y1 side) of the slide attachment direction. Upon the slide attachment of the surgical instrument to the adaptor, the pair of inclined surfaces 49 comes in contact with the drive transmission members 62a and 62b to move the drive transmission members 62a and 62b with respect to the surgical instrument attachment surface 60b toward the robot arm 21a side (the Z2 side) along the vertical direction. That is, upon the slide attachment of the surgical instrument 40 to the adaptor 60, the pair of inclined surfaces 49 comes in contact with the drive transmission members 62a and 62b to move the drive transmission members 62a and 62b with respect to the arm attachment surface 60a and the surgical instrument attachment surface 60b of the adaptor 60 in the vertical direction (the Z2 side), and thus to move the first members 621 of the drive transmission members 62a and 62b toward the robot arm 21a side (the Z2 side).

Accordingly, upon the slide attachment, the pair of inclined surfaces 49 enhances movements of the drive transmission members 62a and 62b with respect to the surgical instrument attachment surface 60b toward the robot arm 21 side (the Z2 side) along the vertical direction. As a result, a force needed upon the attachment of the surgical instrument 40 to the adaptor 60 can be decreased, and thus the surgical instrument 40 can be smoothly attached to the adaptor 60.

Each of the inclined surfaces 49 is formed to be substantially flat. Each of the inclined surfaces 49 is provided being inclined with respect to the adaptor attachment surface 40a. Specifically, each of the inclined surfaces 49 is inclined down to the side (the Z1 side) opposite to the robot arm 21a side toward the leading side (the Y1 side) of the slide attachment direction. It may be preferable that an inclination angle 81 (see FIG. 8) of the inclined surface 49 is greater than 0 degrees and not greater than 45 degrees. Accordingly, compared to a case where the inclination angle 81 of the inclined surface 49 is greater than 45 degrees, a force can be easily applied toward the robot arm 21a side (the Z2 side) along the perpendicular direction with respect to the surgical instrument attachment surface 60b, and thus the drive transmission members 62a and 62b can be easily moved toward the robot arm 21a side (the Z2 side) along the perpendicular direction. The inclination angle 81 of the inclined surface 49 may be approximately 7 degrees, for example.

The inclined surfaces 49 are arranged in the X direction such that the precedence guide groove 47 is provided between the inclined surfaces 49. The inclined surface 49 on the X1 side is configured to move the drive transmission members 62a and 62b on the X1 side toward the robot arm 21a side (the Z2 side) along the perpendicular direction with respect to the surgical instrument attachment surface 60b. The inclined surface 49 on the X2 side is configured to move the drive transmission members 62a and 62b on the X2 side toward the robot arm 21a side (the Z2 side) along the perpendicular direction with respect to the surgical instrument attachment surface 60b.

That is, the inclined surfaces 49 are provided at positions corresponding to the driven transmission members 62a and 62b. Specifically, the inclined surface 49 on the X1 side is provided at a position corresponding to the driven transmission members 62a and 62b on the X1 side. The inclined surface 49 on the X2 side is provided at a position corresponding to the driven transmission members 62a and 62b on the X2 side. Each of the pair of inclined surfaces 49 is formed wider than the corresponding drive transmission member 62a, 62b in the widthwise direction (the X direction) substantially orthogonal to the slide attachment direction. That is, a width W1 of the inclined surface 49 in the X direction is greater than a width W2 (see FIG. 10) of the drive transmission members 62a and 62b. Accordingly, even if the surgical instrument 40 rattles in the width direction substantially orthogonal to the slide attachment direction upon the slide attachment, the inclined surfaces 49 and the drive transmission members 62a and 62b can be reliably brought into contact with each other.

The pair of guided portions 40c is provided on the adaptor attachment surface 40a of the base 40b. Specifically, the pair of guided portions 40c is formed so as to protrude toward the adaptor 60 side (the Z2 side) from the adaptor attachment surface 40a of the base 40b, and is configured to be guided by the precedence guide portion 67 of the adaptor 60 upon the slide attachment. With this configuration, by sliding the guided portions 40c along the precedence guide portion 67, the surgical instrument 40 can be easily slid in the slide attachment direction.

The pair of guided portions 40c is provided at an outer periphery edge portion of the adaptor attachment surface 40a of the base 40b. Specifically, the pair of guided portions 40c is provided on outer side than the pair of the guide grooves 45. The guided portions 40c are provided being opposed to each other in the X direction. Each of the guided portions 40c is provided to extend along the Y direction. The pair of guided portions 40c are configured to be guided by the inner surfaces of the pair of guided portions 40c in the X direction being in contact with the outer surfaces of the precedence guide portion 67 in the X direction. The pair of guided portions 40c is a skirt portion formed in a skirt shape.

The pair of engagement tabs 40d is provided to the base 40b. Specifically, the pair of engagement tabs 40d is provided at a portion of the base 40b on the side (the Y2 side) opposite to the slide attachment direction. The pair of engagement tabs 40d is formed to protrude toward the adaptor 60 side (the Z2 side) from the adaptor attachment surface 40a of the base 40b. The pair of engagement tabs 40d is inserted to and thus engaged with the pair of engagement holes 68 of the adaptor 60. Accordingly, by means of the pair of engagement tabs 40d and the pair of engagement holes 68 of the adaptor 60, the engagement strength between the surgical instrument 40 and the adaptor 60 can be increased, and thus the surgical instrument 40 can be made difficult to come off from the adaptor 60.

The engagement tabs 40d are opposed to each other in the X direction.

Specifically, the engagement tabs 40d are opposed to each other in the X direction such that the electrode array 48 is provided between the engagement tabs 40d. In a state where the surgical instrument 40 is attached to the adaptor 60, the pair of the engagement tabs 40d is engaged with the pair of the engagement holes 68, and thus the surgical instrument 40 is connected to the adaptor 60 with preventing detachment of the surgical instrument 40 from the adaptor 60 in the Z direction.

A pair of engagement holes 40e is provided to the base 40b. Specifically, the pair of engagement holes 40e is provided at a portion of the base 40b on the leading side (the Y1 side) of the slide attachment direction. The pair of engagement holes 40e is formed to be recessed toward the side (the Y2 side) opposite to the slide attachment direction. The pair of engagement holes 40e is inserted to and thus engaged with the pair of engagement tabs 69 of the adaptor 60 respectively. Accordingly, by means of the pair of engagement holes 40e and the pair of engagement tabs 69 of the adaptor 60, the engagement strength between the surgical instrument 40 and the adaptor 60 can be further increased, and thus the surgical instrument 40 can be made more difficult to come off from the adaptor 60.

The pair of engagement holes 40e are opposed to each other in the X direction. Specifically, the engagement holes 40e are opposed to each other in the X direction such that the precedence guide groove 47 is provided between the engagement holes 40e. Specifically, in a state where the surgical instrument 40 is attached to the adaptor 60, the pair of the engagement holes 40e is engaged with the pair of the engagement tabs 69, and thus the surgical instrument 40 is connected to the adaptor 60 with preventing detachment of the surgical instrument 40 from the adaptor 60 in the Z direction.

As illustrated in FIG. 4, the adaptor 60 is provided to detachably connect the surgical instrument 40 to the robot arm 21a of the robotic surgical system 100.

The drive transmission members 62a and 62b are rotatably provided in the base 61. Specifically, the drive transmission members 62a and 62b are provided to be rotatable about rotational axes thereof extending in the Z direction. The drive transmission members 62a and 62b transmit driving force of the rotation drive parts 212 of the robot arm 21a to the driven members 44b and 44a of the surgical instrument 40. The number of the drive transmission members 62a and 62b provided is plural corresponding to the number of the driven members 44b and 44a of the surgical instrument 40. The drive transmission members 62a and 62b are respectively arranged in positions corresponding to the driven members 44b and 44a of the surgical instrument 40. In a state where the surgical instrument 40 is not attached to the adaptor 60, the Z1 side surfaces of the drive transmission member 62a and 62b are protruded toward the surgical instrument 40 side (the Z1 side) beyond the surgical instrument attachment surface 60b.

Figure 7:
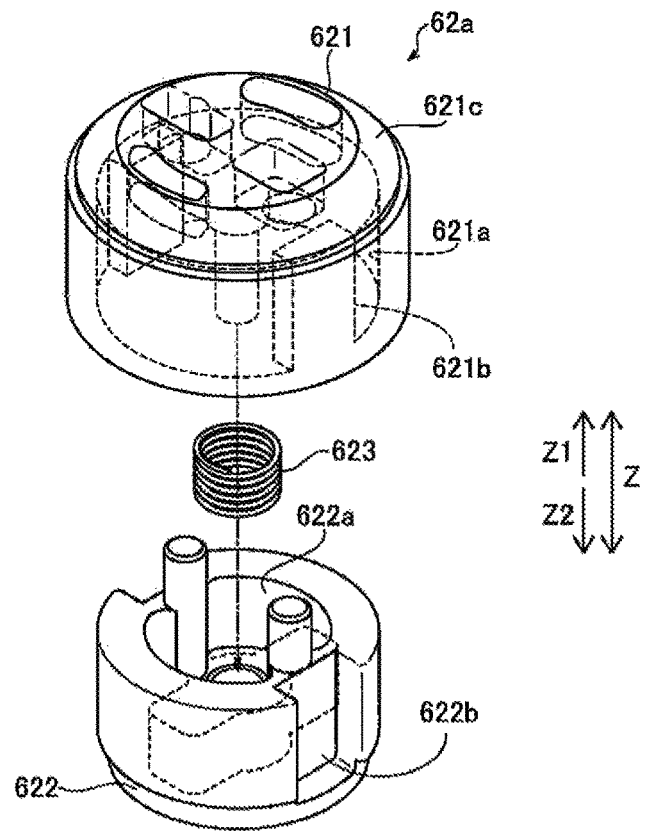
FIG. 7 is a diagram illustrating an exploded perspective view of a drive transmission member of the adaptor according to an embodiment.
Figure 8:
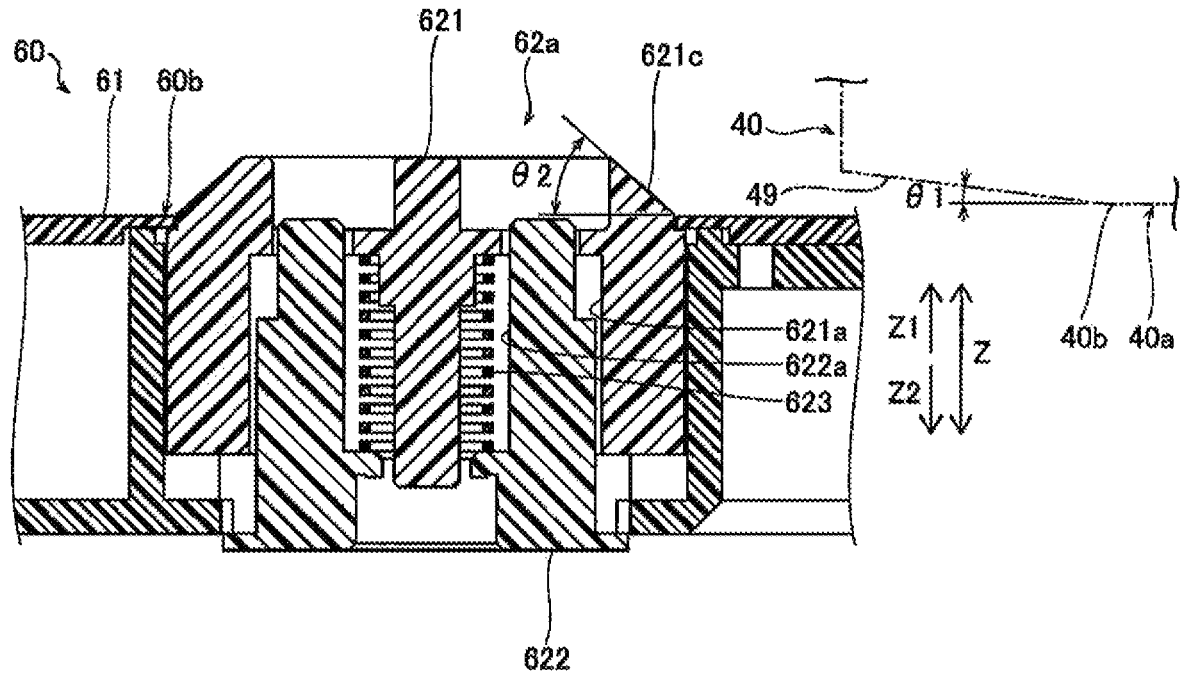
FIG. 8 is a diagram illustrating a schematic cross sectional view of a base and the drive transmission member of the adaptor according to an embodiment.

The drive transmission members 62 and 62b are provided to be movable in the perpendicular direction (the Z direction) with respect to the surgical instrument attachment surface 60b. Specifically, as illustrated in FIGS. 7 and 8, each drive transmission member 62a includes the first member 621 and the second member 622, wherein the second member 622 is provided movably with respect to the first member 621 with a bias member 623 interposed in between. The first member 621 includes a recess portion 621a in which the second member 622 is fitted, engagement portions 621b engaged with the second member 622, and an inclined surface 621c. The second member 622 includes a recess portion 622a in which the bias member 623 is accommodated and engagement portions 622b engaged with the first member 621. The first member 621 and the second member 622 are fitted to each other in the Z direction with the bias member 623 interposed in between. The first member 621 is positioned on the surgical instrument attachment surface 60b side (in the Z1 side). The second member 622 is positioned on the arm attachment surface 60a side (in the Z2 side). The bias member 623 biases the first member 621 toward the Z1 side with respect to the second member 622. For example, the bias member 623 is configured as a compress coil spring. Note that, the drive transmission member 62*b* has the same configuration as the drive transmission member 62*a* except that the shape of a portion of the drive transmission member 62*b* that engages with the driven member 44*a* of the surgical instrument 40 is different from that of the drive transmission member 62*a*. The inclined surface 621*c* is an example of an inclined surface of the adaptor or an adaptor side inclined surface.

The first member 621 is arranged movably with respect to the base 61 in the Z direction. This makes it possible to move the first members 621 of the drive transmission members 62*a* and 62*b* downward in the Z2 direction to prevent interference with the slide movement of the surgical instrument 40 upon sliding the surgical instrument 40 to attach the surgical instrument 40 to the adaptor 60. Specifically, the inclined surface 621*c* of the first member 621 is configured, upon the slide attachment, to come in contact with the inclined surface 49 of the surgical instrument 40. Accordingly, the inclined surfaces 621*c* and the inclined surfaces 49 come in contact with each other upon the slide attachment, and this further enhances movements of the drive transmission members 62*a* and 62*b* toward the robot arm 21 side (the Z2 side) along the direction perpendicular to the surgical instrument attachment surface 60*b* upon the slide attachment. Note that in FIG. 8, the surgical instrument 40 is illustrated by the chain double-dashed line for easy understanding.

The inclined surface 621*c* is formed along the periphery edge portion of the first member 621 in a circular shape. The inclined surface 621*c* is inclined with respect to the upper surface of the first member 621 (the surface of the drive transmission member on the surgical instrument side). Specifically, the inclined surface 621*c* is inclined down to the robot arm 21*a* side (the Z2 side) toward a radial direction from the center of the first member 621 to the periphery side of the first member 621. It may be preferable that an inclination angle 82 of the inclined surface 621*c* is greater than the inclination angle 81 of the inclined surface 49 and not greater than 90 degrees. Accordingly, the inclined surfaces 49 can easily come in contact with the inclined surfaces 621*c*, and this further enhances movements of the drive transmission members 62*a* and 62*b* toward the robot arm 21 side (the Z2 side) along the direction perpendicular to the surgical instrument attachment surface 60*b* upon the slide attachment. The inclination angle 82 of the inclined surface 621*c* may be approximately 60 degrees, for example.

The first member 621 is configured to rotate in accordance with the rotation of the second member 622 about the rotation axis in the Z direction. Specifically, the first member 621 and the second member 622 are configured such that the engagement portions 621*b* provided in an inner circumferential portion of the first member 621 and the engagement portions 622*b* provided in an outer circumferential portion of the second member 622 are engaged with each other. The engagement portions 621*b* of the first member 621 are formed to protrude inward from the recess portion 621*a*. The engagement portions 622*b* of the second member 622 are formed to be recessed inward from the outer circumferential portion of the second member 622. The engagement portions 621*b* of the first member 621 and the engagement portions 622*b* of the second member 622 are configured to be engaged with each other even when the first member 621 is moved with respect to the second member 622 in the Z direction. Specifically, the first member 621 is configured to be rotated with the second member 622 regardless of the position of the first member 621 with respect to the second member 622 in the Z direction. Therefore, when the second member 622 is rotated in accordance with the rotation of the rotation drive part 212 of the robot arm 21*a*, the first member 621 is rotated together. Consequently, the rotations of the rotation drive parts 212 of the robot arm 21*a* are transmitted to the driven members 44*a* and 44*b* of the surgical instrument 40, engaged with the first members 621 of the drive transmission members 62*a* and 62*b* of the adaptor.

Figure 9:
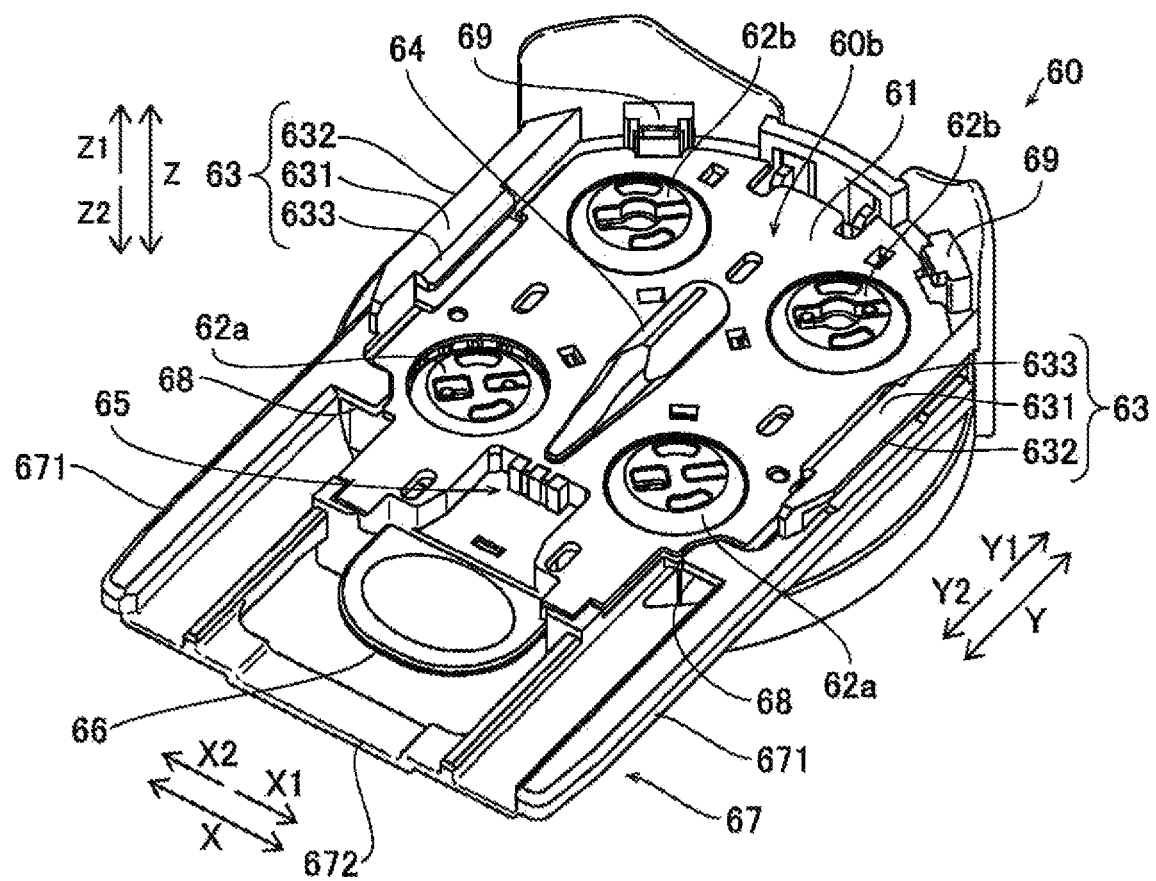
FIG. 9 is a diagram illustrating a perspective view of the adaptor according to an embodiment.
Figure 10:
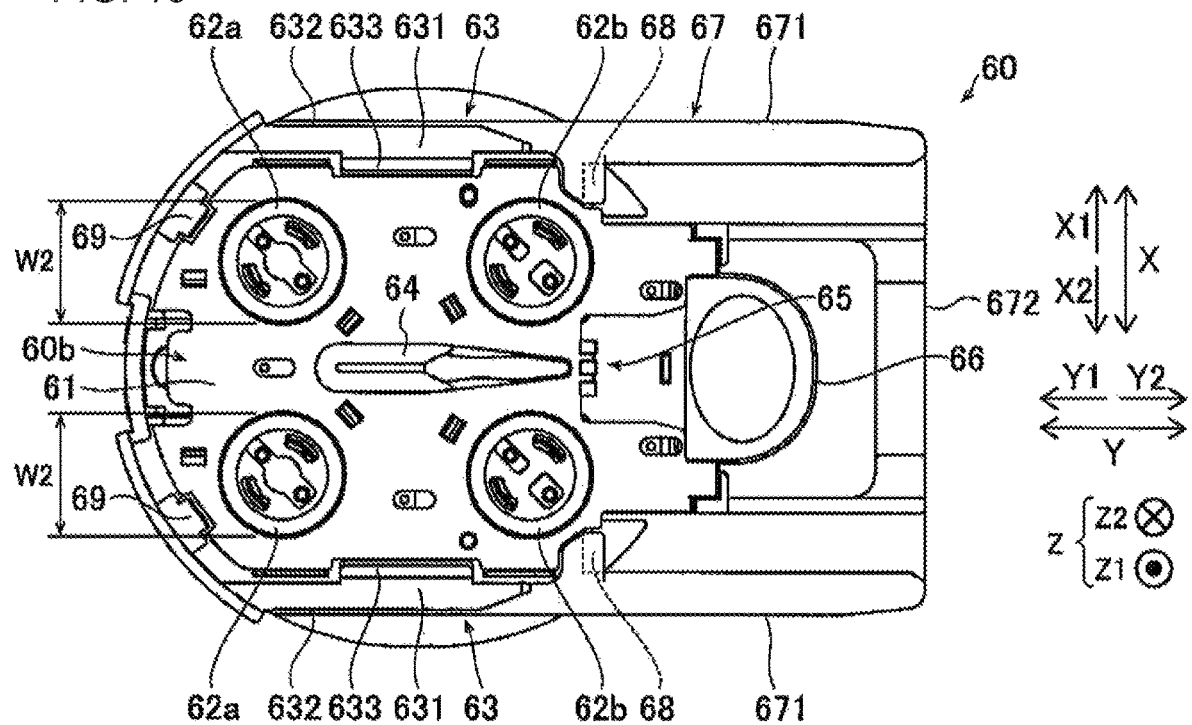
FIG. 10 is a diagram illustrating a plan view of the adaptor according to an embodiment as seen from the Z1 side.

As illustrated in FIGS. 9 and 10, the guide rails 63 are provided on the surgical instrument attachment surface 60*b*. Each of the guide rails 63 is provided to extend along the Y direction. The two guide rails 63 are provided to be opposed to each other in the X direction. The pair of guide rails 63 is provided to correspond to the pair of guide grooves 45 provided substantially parallel to each other on the adaptor attachment surface 40*a* of the surgical instrument 40. The pair of guide rails 63 of the surgical instrument attachment surface 60*b* is configured to slidably guide the pair of guide grooves 45 of the adaptor attachment surface 40*a*, in the Y direction, thereby guiding the surgical instrument 40 to the position where the drive transmission members 62*a* and 62*b* correspond to the driven members 44*b* and 44*a* provided on the adaptor attachment surface 40*a*.

Each of the guide rails 63 includes a rail part 631, a jut part 632, and a tab part 633. The rail part 631 is formed to extend in the Y direction. The rail part 631 is configured to be inserted into the guide groove 45 of the surgical instrument 40 and guide the movement of the surgical instrument 40 with respect to the adaptor 60.

The jut part 632 is formed to jut in the X direction from the rail part 631. Specifically, in the guide rail 63 on the X1 side, the jut part 632 is provided on the X1 side of the rail part 631, whereas in the guide rail 63 on the X2 side, the jut part 632 is arranged on the X2 side of the rail part 631.

The tab part 633 is formed to project in the X direction from the rail part 631. Specifically, in the guide rail 63 on the X1 side, the tab part 633 is provided on the X2 side of the rail part 631, whereas in the guide rails 63 on the X2 side, the tab part 633 is provided on the X1 side of the rail part 631. That is, the jut part 632 is provided to each of the rail parts 631 on the opposite side of the tab part 633. The jut part 632 is provided on the outer side in the X direction of the rail part 631. The tab part 633 is arranged in the inner side in the X direction of the rail part 631.

The jut part 632 is configured to be engaged with a restriction portion 451 (see FIG. 6) provided in the guide groove 45 of the surgical instrument 40. The engagement of the jut part 632 with the restriction portion 451 enables the connection between the surgical instrument 40 and the adaptor 60 and prevents detachment of the surgical instrument 40 from the adaptor 60 in the Z direction.

The tab part 633 is engaged with an engagement hole 461 (see FIG. 6) provided in the guide groove 45 of the surgical instrument 40. Specifically, the tab part 633 is engaged with the engagement hole 461 provided in the movable member 46 defining the guide groove 45. The engagement of the tab part 633 with the engagement hole 461 enables positioning and fixing of the surgical instrument 40 guided by the guide rail 63 with respect to the adaptor 60. Specifically, the engagement of the tab part 633 with the engagement hole 461 enables positioning of the surgical instrument 40 in the Y direction with respect to the adaptor 60 and fixing (locking) of the surgical instrument 40 to the adaptor 60 to prevent the detachment of the surgical instrument 40 from the adaptor 60 in the Y direction.

The precedence guide rail 64 is provided on the surgical instrument attachment surface 60*b*. The precedence guide rail 64 is provided to extend along the Y direction. The precedence guide rail 64 is provided between the pair of guide rails 63. The precedence guide rail 64 is formed to extend substantially parallel to the guide rails 63. The precedence guide rail 64 is provided in the substantial center in the X direction of the surgical instrument attachment surface 60b. The precedence guide rail 64 is provided corresponding to the precedence guide groove 47 provided on the adaptor attachment surface 40a. Specifically, the precedence guide rail 64 guides the surgical instrument 40 before the pair of guide rails 63 guides the surgical instrument 40.

The electrode array 65 is connected to the electrode array 48 of the surgical instrument 40 and the robot arm 21a.

As illustrated in FIGS. 4 and 5, the arm engagement portion 66 is engaged with the engagement portions 213 of the robot arm 21a. Specifically, the arm engagement portion 66 is engaged with the engagement portions 213 that are inserted in the arm engagement holes 60c provided in the arm attachment surface 60a. The arm engagement portion 66 can be moved in the Y direction. The arm engagement portion 66 is biased in the Y1 direction by a bias member. The engagement of the arm engagement portion 66 with the engagement portions 213 is made by moving the arm engagement portion 66 in the Y1 direction. On the other hand, the engagement of the arm engagement portion 66 with the engagement portions 213 is released by moving the arm engagement portion 66 in the Y2 direction.

The number of the arm engagement holes 60c provided is plural. That is, the adaptor 60 is fixed to the robot arm 21a by engagement of the plural positions. For example, five arm engagement holes 60c are provided. The arm engagement holes 60c are provided at equal intervals along a circumferential direction of the arm attachment surface 60a.

The positioning holes 60d are provided in the arm attachment surface 60a. The bosses 214 of the robot arm 21a are fitted to the positioning holes 60d. The number of the positioning holes 60d provided is plural. The positioning holes 60d are provided near an end portion in the Y1 side of the arm attachment surface 60a.

As illustrated in FIGS. 9 and 10, the precedence guide portion 67 is provided along the slide attachment direction and is projected from the base 61 in a direction (the Y2 direction) opposite to the slide attachment direction. The precedence guide portion 67 is provided to guide the surgical instrument 40 upon the slide attachment of the surgical instrument 40 to the adaptor 60. With this configuration, the precedence guide rail 64 can guide the surgical instrument 40 before the pair of guide rails 63 guides the surgical instrument 40, and thus the surgical instrument 40 can be easily guided to the attachment position of the surgical instrument 40 to the adaptor 60.

That is, the precedence guide portion 67 is provided so as to correspond to the pair of the guided portions 40c of the surgical instrument 40. The precedence guide portion 67 is configured to guide the surgical instrument 40 while the outer surfaces of the precedence guide portion 67 in the X direction are in contact with the pair of guided portions 40c. The precedence guide portion 67 is configured to guide the surgical instrument 40 before the pair of guide rails 63 guides the surgical instrument 40. The precedence guide portion 67 is configured to guide the surgical instrument 40 before the inclined surfaces 49 come in contact with the drive transmission members 62a. With this configuration, the inclined surfaces 49 can be brought into contact with the drive transmission members 62a in the state where the precedence guide portion 67 guides the surgical instrument 40. Thus, the inclined surfaces 49 can be brought into stable contact with the drive transmission members 62a. Each of the inclined surfaces 49 has such a length that the inclined surface 49 is not contact with the drive transmission member 62a upon the start of guiding the surgical instrument 40 by the precedence guide portion 67.

The precedence guide portion 67 includes a pair of guide bars 671 and a guide bar connection portion 672 that connects the pair of guide bars 671. Each of the guide bars 671 is provided to extend along the Y direction. The guide bars 671 are opposed to each other in the X direction. Specifically, the guide bars 671 are opposed to each other in the X direction such that the arm engagement portion 66 is provided between the guide bars 671. The pair of guide bars 671 is provided to correspond to the pair of guided portions 40c.

The guide bar 671 on the X1 side is configured to guide the guided portion 40c on the X1 side. Specifically, the guide bar 671 on the X1 side includes a X1 side surface that guides the guided portion 40c on the X1 side. The guide bar 671 on the X2 side is configured to guide the guided portion 40c on the X2 side. Specifically, the guide bar 671 on the X2 side includes a X2 side surface that guides the guided portion 40c on the X2 side.

A guide bar connection portion is provided to connect the pair of guide bars 671. Specifically, the guide bar connection portion 672 is provided to connect the Y2 side ends of the pair of guide bars 671. The guide bar connection portion 672 is provided to extend along the X direction. The guide bar connection portion 672 improves the mechanical strength of the pair of guide bars 671.

The pair of engagement holes 68 is provided to the base 61. Specifically, the pair of engagement hole 68 is provided at a position of the base 40b on the side (the Y2 side) opposite to the slide attachment direction. The pair of engagement holes 68 is formed to be recessed toward the leading side (the Y1 side) of the slide attachment direction. The pair of engagement holes 68 is inserted to and thus engaged with the pair of engagement tabs 40d of the surgical instrument 40. The pair of engagement holes 68 is provided to correspond to the pair of engagement tabs 40d. The engagement holes 68 are opposed to each other in the X direction. Specifically, the engagement holes 68 are opposed to each other in the X direction such that the electrode array 65 is provided between the engagement holes 68.

The pair of engagement tabs 69 is provided to the base 61. Specifically, the pair of engagement tabs 69 is provided at a portion of the base 61 on the leading side (the Y1 side) of the slide attachment direction side. The pair of engagement tabs 69 is formed to protrude toward the surgical instrument 40 side (the Z1 side) from the surgical instrument attachment surface 60b of the adaptor 60. The pair of engagement tabs 69 is configured to be inserted to and thus engaged with the pair of engagement holes 40e of the surgical instrument 40. The pair of engagement tabs 69 is provided to correspond to the pair of engagement holes 40e. The engagement tabs 69 are opposed to each other in the X direction.

(Attachment of Surgical Instrument to Robot Arm)

Figure 11:
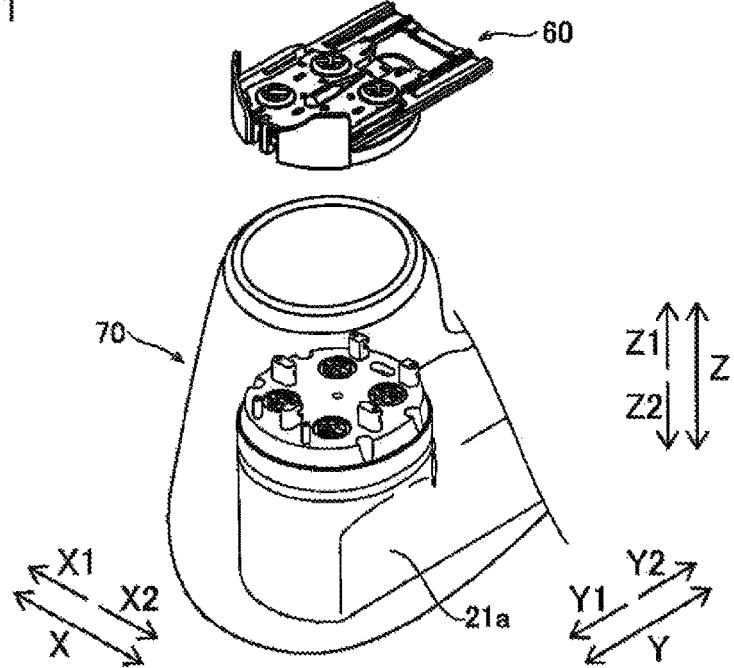
FIG. 11 is a diagram illustrating a first explanatory view for explaining attachment of the adaptor to the robot arm according to an embodiment.
Figure 12:
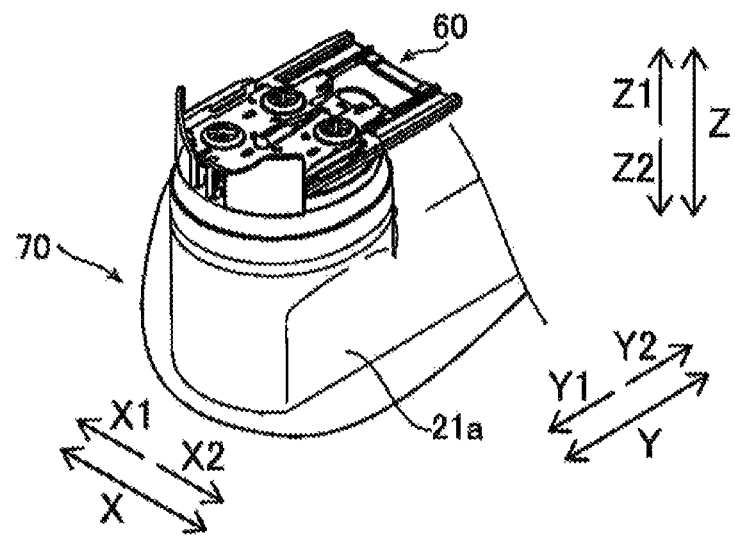
FIG. 12 is a diagram illustrating a second explanatory view for explaining the attachment of the adaptor to the robot arm according to an embodiment.
Figure 13:
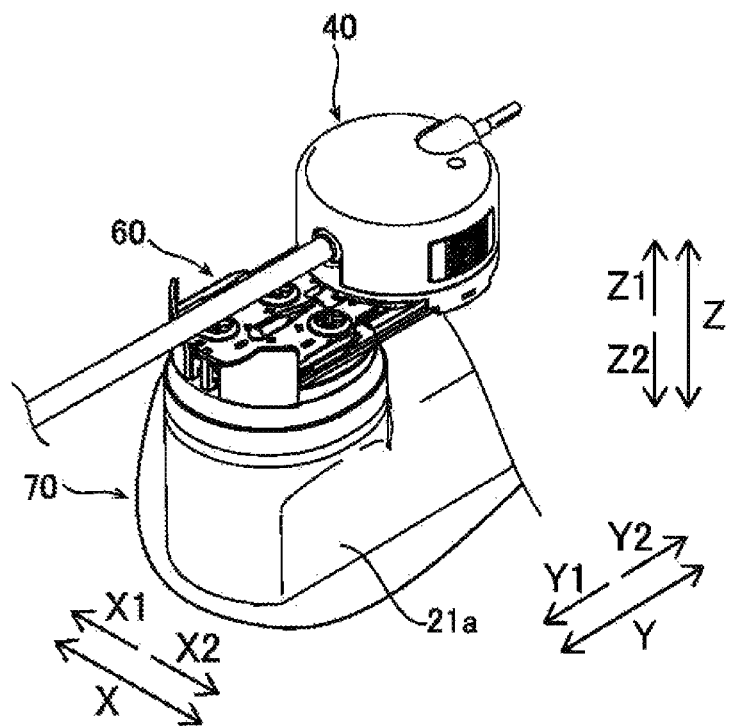
FIG. 13 is a diagram illustrating an explanatory view for explaining attachment of the surgical instrument to the adaptor according to an embodiment.

With reference to FIGS. 11 to 13, the attachment of the surgical instrument 40 to the robot arm 21a according to an embodiment is described.

As illustrated in FIGS. 11 and 12, the adaptor 60 is attached to the robot arm 21a with the robot arm 21 being covered by the drape 70. The adaptor 60 is moved in the Z direction with respect to the robot arm 21a to be attached to the robot arm 21a. As illustrated in FIG. 13, the surgical instrument 40 is attached to the adaptor 60 attached to the robot arm 21a. The surgical instrument 40 is moved in the Y direction along the precedence guide portion 67, the precedence guide rail 64, and the guide rails 63 of the adaptor 60 and thereby attached to the adaptor 60.

Specifically, first, the surgical instrument 40 is positioned on the Z1 side of the adaptor 60 in such a manner that the guided portions 40c of the surgical instrument 40 are in contact with the precedence guide portion 67 of the adaptor 60. Next, the surgical instrument 40 is moved in the Y1 direction while the precedence guide portion 67 guides the guided portions 40c. Then, the surgical instrument 40 is further moved in the Y1 direction while the precedence guide rail 64 guides the precedence guide groove 47 and then the guide rails 63 guide the guide grooves 45, so that the surgical instrument 40 is moved to the attachment completion position. In this procedure, the inclined surfaces 49 of the surgical instrument 40 come in contact with the drive transmission members 62a and 62b, and thus the drive transmission members 62a and 62b are moved toward the Z2 side.

When the surgical instrument 40 is attached to the adaptor 60, the restriction portions 451 of the guide grooves 45 of the surgical instrument 40 and the jut parts of the guide rails 63 of the adaptor 60 are engaged with each other and the engagement holes 461 of the guide grooves 45 and the tab parts 633 of the guide rails 63 of the adaptor 60 are engaged with each other. Further, the engagement tabs 40d of the surgical instrument 40 and the engagement holes 68 of the adaptor 60 are engaged with each other and the engagement holes 40e of the surgical instrument 40 and the engagement tabs 69 of the adaptor 60 are engaged with each other.

In this way, the surgical instrument 40 is attached to the robot arm 21a through the adaptor 60.

(Modifications)

It should be understood that one or more embodiments described above are illustrated by way of example in every respect and not limit the invention. The scope of the invention is defined not by the above-described one or more embodiments, but by the scope of claims, and includes all modifications (variations) within equivalent meaning and scope to those of the claims.

For example, in an embodiment described above, the drive transmission members of the adaptor include the inclined surfaces with which the inclined surfaces of the surgical instrument come in contact, upon the slide attachment. However, the disclosure is not limited to this. In the disclosure, the drive transmission members of the adaptor may not include the inclined surfaces with which the inclined surfaces of the surgical instrument come in contact, upon the slide attachment.

Further, in an embodiment described above, the inclination angle of the inclined surfaces of the adaptor is greater than that of the inclined surfaces of the surgical instrument. However, the disclosure is not limited to this. In the disclosure, the inclination angle of the inclined surfaces of the adaptor may be equal to or less than that of the inclined surfaces of the surgical instrument.

In an embodiment described above, the inclination angle of the inclined surfaces of the surgical instrument is not greater than 45 degree. However, the disclosure is not limited to this. In the disclosure, the inclination angle of the inclined surfaces of the surgical instrument may be greater than 45 degree.

In an embodiment described above, the pair (two) of inclined surfaces are provided to the surgical instrument. However, the disclosure is not limited to this. In the disclosure, the number of the inclined surface(s) of the surgical instrument may be one.

In an embodiment described above, the inclined surfaces of the surgical instrument are wider than those of the drive transmission members. However, the disclosure is not limited to this. In the disclosure, the widths of the inclined surfaces of the surgical instrument may be equal or less than those of the drive transmission members.

In an embodiment described above, the number of the drive transmission members provided to the robotic surgical apparatus is four. However, the disclosure is not limited to this. In the disclosure, the number of the drive transmission members provided to the robotic surgical apparatus may be more than one other than four.

In an embodiment described above, the adaptor includes the precedence guide portion. However, the disclosure is not limited to this. In the disclosure, the adaptor may not include the precedence guide portion.

In an embodiment described above, the slide attachment direction is substantially parallel to the extending direction of the shaft of the surgical instrument. However, the disclosure is not limited to this. In the disclosure, the slide attachment direction may intersect with the extending direction of the shaft of the surgical instrument.

In an embodiment described above, the adaptor and the drape are provided independently of each other. However, the disclosure is not limited thereto. In the disclosure, the adaptor and the drape may be integrally provided.

In an embodiment described above, the adaptor includes the precedence guide rail. However, the disclosure is not limited to this. In the disclosure, the adaptor may not include the precedence guide rail.

In an embodiment described above, the surgical instrument is slid along the precedence guide portion with the guided portions being in contact with the precedence guide portion. However, the disclosure is not limited to this. In the disclosure, the surgical instrument may be slid along the precedence guide portion with a pair of engagement tabs of the surgical instrument being in contact with the precedence guide portion.

The invention claimed is:

1. A robotic surgical apparatus comprising:
a robot arm;
an adaptor that is attached to the robot arm; and
a surgical instrument that is attached to the adaptor by sliding the surgical instrument with respect to the adaptor, the surgical instrument including a driven member, wherein
the adaptor includes: an adaptor base including an arm attachment surface which is attached to the robot arm and a surgical instrument attachment surface which is provided on an opposite side of the arm attachment surface and to which the surgical instrument is attached; and a drive transmission member provided being movable in a direction perpendicular to the surgical instrument attachment surface of the adaptor base and configured to be engaged with the driven member of the surgical instrument at a position where the surgical instrument is attached to the adaptor to transmit a driving force from the robot arm to the driven member of the surgical instrument, the drive transmission member being provided in the adaptor base such that a part of the drive transmission member is protruded out of the adaptor base from the surgical instrument attachment surface of the adaptor base,
the surgical instrument includes a surgical instrument base including an adaptor attachment surface to be attached to the adaptor, and the surgical instrument base includes an inclined surface of the surgical instrument configured, upon slide attachment of the surgical instrument to the adaptor, to come in contact with the protruded part of the drive transmission member to move the drive transmission member toward the robot arm side in the direction perpendicular to the surgical instrument attachment surface of the adaptor before the drive transmission member is engaged with the driven member of the surgical instrument, so as to prevent the protruded part of the drive transmission member from interfering with the slide attachment of the surgical instrument.

2. The robotic surgical apparatus according to claim 1, wherein the drive transmission member of the adaptor includes an inclined surface of the adaptor configured, upon the slide attachment, to come in contact with the inclined surface of the surgical instrument.

3. The robotic surgical apparatus according to claim 2, wherein an inclination angle of the inclined surface of the adaptor with respect to a surface of the drive transmission member on the surgical instrument side is greater than an inclination angle of the inclined surface of the surgical instrument with respect to the adaptor attachment surface of the surgical instrument.

4. The robotic surgical apparatus according to claim 3, wherein the drive transmission member includes: a first member being movable in the direction perpendicular to the surgical instrument attachment surface; a second member provided being movable with respect to the first member; and a bias member provided between the first member and the second member, and a surface of the first member on the surgical instrument side comprises the surface of the drive transmission member on the surgical instrument side.

5. The robotic surgical apparatus according to claim 1, wherein the drive transmission member includes: a first member being movable in the direction perpendicular to the surgical instrument attachment surface; a second member provided being movable with respect to the first member; and a bias member provided between the first member and the second member.

6. The robotic surgical apparatus according to claim 1, wherein an inclination angle of the inclined surface of the surgical instrument with respect to the adaptor attachment surface of the surgical instrument is greater than 0 degrees and not greater than 45 degrees.

7. The robotic surgical apparatus according to claim 1, wherein the inclined surface of the surgical instrument is wider than the drive transmission member in a widthwise direction substantially orthogonal to a direction of the slide attachment of the surgical instrument to the adaptor.

8. The robotic surgical apparatus according to claim 1, wherein the adaptor further includes a precedence guide portion protruded from the adaptor base in a direction opposite to a direction of the slide attachment of the surgical instrument to the adaptor and configured, upon the slide attachment of the surgical instrument to the adaptor, to guide the surgical instrument.

9. The robotic surgical apparatus according to claim 8, wherein the surgical instrument base further includes a guided portion protruded toward the adaptor side from the adaptor attachment surface and configured, upon the slide attachment, to be guided by the precedence guide portion of the adaptor.

10. The robotic surgical apparatus according to claim 8, wherein the precedence guide portion of the adaptor includes a pair of guide bars protruded from the adaptor base in the direction opposite to the slide attachment direction and a guide bar connection portion connecting the pair of guide bars.

11. The robotic surgical apparatus according to claim 10, wherein the surgical instrument base further includes a pair of guided portions protruded toward the adaptor side from the adaptor attachment surface and configured, upon the slide attachment, to be guided by the pair of guide bars.

12. The robotic surgical apparatus according to claim 1, wherein the adaptor attachment surface of the surgical instrument includes a pair of guide grooves extending along a direction of the slide attachment of the surgical instrument to the adaptor, and the surgical instrument attachment surface of the adaptor includes a pair of guide rails to be inserted in the pair of guide grooves.

13. The robotic surgical apparatus according to claim 12, wherein the adaptor attachment surface of the surgical instrument includes a precedence guide groove provided between the pair of guide grooves and extending along the slide attachment direction, the surgical instrument attachment surface of the adaptor includes a precedence guide rail provided between the pair of guide rails and configured to guide the precedence guide groove, and the precedence guide rail guides the surgical instrument before the pair of guide rails guides the surgical instrument.

14. The robotic surgical apparatus according to claim 1, wherein the surgical instrument base includes, at a portion of the surgical instrument base on a side opposite to a direction of the slide attachment of the surgical instrument to the adaptor, a first engagement portion of the surgical instrument protruded toward the adaptor side from the adaptor attachment surface, and the adaptor base includes, at a portion of the adaptor base on the side opposite to the slide attachment direction, a first engagement portion of the adaptor configured to be engaged with the first engagement portion of the surgical instrument.

15. The robotic surgical apparatus according to claim 14, wherein the adaptor base includes, at a portion of the adaptor base on a leading side of the slide attachment direction, a second engagement portion of the adaptor protruded toward the surgical instrument side from the surgical instrument attachment surface, and the surgical instrument base includes, at a portion of the surgical instrument base on the leading side of the slide attachment direction, a second engagement portion of the surgical instrument configured to be engaged with the second engagement portion of the adaptor.

16. The robotic surgical apparatus according to claim 1, wherein
a direction of the slide attachment of the surgical instrument to the adaptor is substantially parallel to a direction in which a shaft of the surgical instrument extends.

17. The robotic surgical apparatus according to claim 1, wherein
the adaptor is a drape adaptor configured to sandwich a drape between the adaptor and the robot arm.

18. The robotic surgical apparatus according to claim 1, wherein
the inclined surface of the surgical instrument is provided at a portion of the adaptor attachment surface of the surgical instrument base on a leading side of a direction of the slide attachment of the surgical instrument to the adaptor.

19. A surgical instrument to be attached to a surgical instrument attachment surface of an adaptor provided on an opposite side of an arm attachment surface of the adaptor configured to be attached to a robot arm, by sliding the surgical instrument with respect to the adaptor, comprising:
a surgical instrument base including an adaptor attachment surface to be attached to the adaptor; and
a driven member configured to be engaged with a drive transmission member provided in the adaptor at a position where the surgical instrument is attached to the adaptor, wherein
the drive transmission member of the adaptor is provided in an adaptor base such that a part of the drive transmission member is protruded out of the adaptor base from the surgical instrument attachment surface of the adaptor base,
the drive transmission member of the adaptor being movable in a direction perpendicular to the surgical instrument attachment surface of the adaptor and configured to be engaged with the driven member of the surgical instrument at the position where the surgical instrument is attached to the adaptor so as to transmit a driving force from the robot arm to the driven member of the surgical instrument, and
the surgical instrument base includes an inclined surface of the surgical instrument configured, upon slide attachment of the surgical instrument to the adaptor, to come in contact with the protruded part of the drive transmission member to move the drive transmission member toward the robot arm side in the direction perpendicular to the surgical instrument attachment surface of the adaptor before the drive transmission member is engaged with the driven member of the surgical instrument so as to prevent the protruded part of the drive transmission member from interfering with the slide attachment of the surgical instrument.

20. A method of attaching a surgical instrument to an adaptor attached to a robot arm by sliding the surgical instrument with respect to the adaptor, wherein at a position where the surgical instrument is attached to the adaptor, a drive transmission member provided in the adaptor is engaged with a driven member provided in the surgical instrument to transmit a driving force from the robot arm to the driven member of the surgical instrument, and, before the surgical instrument is attached to the adaptor to engage the drive transmission member of the adaptor with the driven member of the surgical instrument, a part of the drive transmission member is protruded out of an adaptor base from a surgical instrument attachment surface of the adaptor base, the method comprising:
guiding the surgical instrument to move in a direction of slide attachment of the surgical instrument to the adaptor by a precedence guide portion that is protruded from the adaptor base of the adaptor toward a direction opposite to the direction of the slide attachment of the surgical instrument to the adaptor;
bringing an inclined surface of the surgical instrument into contact with the protruded part of the drive transmission member to move the drive transmission member in a direction perpendicular to the slide attachment direction before the drive transmission member is engaged with the driven member of the surgical instrument so as to prevent the protruded part of the drive transmission member from interfering with the slide attachment of the surgical instrument; and
engaging the drive transmission member with the driven member of the surgical instrument at the position where the surgical instrument is attached to the adaptor at an end of the slide attachment of the surgical instrument to the adaptor.

* * * * *